(12) United States Patent
Hiebert

(10) Patent No.: US 8,690,806 B2
(45) Date of Patent: Apr. 8, 2014

(54) SURGICAL POSITIONING SYSTEM

(75) Inventor: Eugene Lloyd Hiebert, Salem, OR (US)

(73) Assignee: Allen Medical Systems, Inc., Batesville, IN (US)

( * ) Notice: Subject to any disclaimer, the term of this patent is extended or adjusted under 35 U.S.C. 154(b) by 546 days.

(21) Appl. No.: 13/011,686

(22) Filed: Jan. 21, 2011

(65) Prior Publication Data

US 2011/0126355 A1    Jun. 2, 2011

Related U.S. Application Data

(63) Continuation-in-part of application No. 12/584,337, filed on Sep. 2, 2009, now Pat. No. 8,469,911.

(51) Int. Cl.
  *A61F 5/00* (2006.01)
(52) U.S. Cl.
  USPC ............................................ 602/13; 128/845
(58) Field of Classification Search
  USPC .......... 128/845, 846, 869–876; 602/5, 19, 13; 5/628, 913
  See application file for complete search history.

(56) References Cited

U.S. PATENT DOCUMENTS

| | | | |
|---|---|---|---|
| 3,212,497 A | 10/1965 | Dickinson | |
| 3,762,404 A * | 10/1973 | Sakita | 602/6 |
| 4,234,982 A | 11/1980 | Bez et al. | |
| 4,657,003 A | 4/1987 | Wirtz | |
| 4,862,879 A * | 9/1989 | Coombs | 602/13 |
| 4,885,811 A | 12/1989 | Hayes | |
| 4,962,769 A | 10/1990 | Garcia | |
| 4,999,867 A | 3/1991 | Toivio et al. | |
| 5,121,756 A | 6/1992 | Koledin | |
| 5,154,185 A | 10/1992 | Latimer et al. | |
| D362,913 S | 10/1995 | Eisenberg et al. | |
| 5,586,348 A | 12/1996 | Toivio et al. | |
| 5,621,934 A | 4/1997 | Olkkonen et al. | |
| 5,626,150 A * | 5/1997 | Johnson et al. | 5/628 |
| 5,634,222 A | 6/1997 | Zwickey | |
| 5,647,079 A | 7/1997 | Hakamium | |
| 5,659,908 A | 8/1997 | Nishino | |
| 5,906,205 A | 5/1999 | Hiebert | |
| 6,318,372 B1 | 11/2001 | Hiebert | |

OTHER PUBLICATIONS

Schroer Manufacturing Company, Shor-line® catalog; "Vacu-Positioner," 3 pp., p. G1 (1987).
Schroer Manufacturing Company, Shore-line® catalog; "Vacu-Positioner," p. F20 Sep. 1998).
Natus, Olympic Papoose Boards, http://www.natus.com/index.cfm?pa . . . , 2 pp. (visited Jun. 17, 2010).
Natus, Olympic Vac-Pac, http://www.natus.com/index.cfm?pa . . . , 2 pp. (visited Jun. 17, 2010).
SW Med-Source, http://www.swmedsource.com/bean . . . , 6 pp. (visited Jun. 17, 2010).

* cited by examiner

*Primary Examiner* — Michael A. Brown
(74) *Attorney, Agent, or Firm* — Barnes & Thornburg LLP

(57) ABSTRACT

A surgical positioning system includes a flexible air-impermeable shell filled with beads that is wrapped against the patient and subjected to a vacuum to hold the patient in place. An air-impermeable top wall can be joined with an air-impermeable bottom wall to define a plurality of chambers. Each of the chambers can include a peripheral edge that extends around the periphery of the respective chamber. The plurality of chambers can include a first shoulder chamber, a second shoulder chamber, and a main chamber.

16 Claims, 13 Drawing Sheets

SURGICAL POSITIONING SYSTEM

CROSS REFERENCE TO RELATED APPLICATION

This application is a continuation-in-part application of U.S. patent application Ser. No. 12/584,337, which was filed on Sep. 2, 2009 now U.S. Pat. No. 8,469,911 and is incorporated herein in its entirety.

FIELD

This invention relates to an improved positioning system for supporting, restraining and/or immobilizing a patient during medical treatment.

BACKGROUND

Vacuum actuated positioning aids or devices are utilized in the operating room for positioning patients in the supine, prone and lateral positions. They are frequently used when the patient is in the lateral position, i.e., on his or her side, for a multitude of surgical procedures, such as brain, chest, kidney, shoulder and hip surgery, to name a few. The devices typically comprise a flexible air impervious bag containing small particles or beads which consolidate into a rigid mass when the bag is evacuated. See, for example, U.S. Pat. No. 3,762,404 to Sakita and U.S. Pat. No. 5,906,205 to Hiebert. Devices according to the Hiebert patent are sold by Hug-U-Vac under the trademark HUG-U-VAC®.

More specifically, devices of this type typically are filled with thousands of tiny, elastically deformable, generally spherical, polystyrene or plastic beads. When the device is in the soft (unevacuated) condition, the beads are free to move around so that the device can be molded to the patient's body. When air is removed (using a vacuum source), atmospheric pressure forces the beads together into a solid mass, positioning yet immobilizing the patient in the selected position. Allowing air back into the device returns it to its initial soft condition, ready for re-use.

These positioning devices, sometimes referred to as bean bag positioners, typically have a generally square or rectangular shape and in some cases are provided with a U-shaped shoulder cutout located centrally along one edge. One line of bean bag and "vacuum pac" positioners is offered by SW Med-Source, P.O. Box 93115, Southlake, Tex. (www.swmedsource.com). SW Med-Source offers gel bean bag positioners as well. Another line of Olympic Vac-Pac® bean bag positioners is offered by Natus Medical Incorporated, 1501 Industrial Road, San Carlos, Calif. (www.natus.com).

Fabric-style devices also are used for positioning patients during exam or treatment. These devices typically are wrapped around one or more sections of the patient, and include one or more wide canvas flaps with adjustable Velcro™ straps. The flaps may be detached/unwrapped to allow a particular area of the patient to be selectively exposed for treatment. See, for example, Natus' Olympic Papoose Boards™ (www.natus.com)

Foam pads and other positioning aids also are used to reduce pressure points and provide patient support during surgery.

There remains however a need for an improved positioning system for surgery in which the patient is in a supine position, especially surgeries in which the patient is supported on an inclined surgery table as, for example, when the patient is in the Trendelenburg, Reverse Trendelenburg or Lateral Oblique positions.

In the Trendelenburg position, the patient is laid flat on her back with her feet above her head. This position may be used during certain laparoscopic and other procedures such as colectomies, hysterectomies, prostatectomies and robotic procedures. In some procedures, the angle of incline is so steep that the patient is in a so-called Steep Trendelenburg position. In the Reverse Trendelenburg position, the patient is tilted in the opposite direction with his head above his feet.

Accordingly, it is desirable to provide an improved positioning system for patients positioned in a supine position during surgery, especially surgeries requiring the patient to be oriented in an inclined position rather than a perfectly horizontal supine position.

It also is desirable to provide an improved positioning system for certain types of surgeries including, for example, laparatomies, laparoscopic procedures, colorectal procedures, gynecological procedures, neurological procedures, cholecystectomies, Nissin Fundoplications and da Vinci procedures.

It is further desirable to provide an improved positioning system for supine patients with better head and neck support.

It is also desirable to provide, at least in some embodiments, an improved positioning system that can be used with bariatric patients.

SUMMARY

In one example, a surgical positioning device for positioning the body of the patient in a selected position includes a flexible and air-impermeable shell having an air-impermeable top wall joined with an air-impermeable bottom wall, the shell defining an air-impermeable outer periphery. The outer periphery of the shell includes an upper edge, a lower edge and opposing first and second lateral edges extending between the upper edge and lower edge, and defines a laterally extending midline extending between the opposing lateral edges. An upper portion of the shell extends between the laterally extending midline and the upper edge. A lower portion of the shell extends between the laterally extending midline and the lower edge. A central region for supporting the patient's torso straddles the laterally extending midline and extends between the upper portion and lower portion. The upper portion includes opposing first and second shoulder support regions positioned laterally outward of the central region and adjacent the upper edge for supporting the patient's respective shoulders.

In another example, the lower edge defines a longitudinally recessed perineal access region for providing access to the patient's perineal region.

In another example, the upper portion includes rounded shoulder portions each having a radius of curvature that generally increases as the shoulder portion extends laterally outwardly toward its respective lateral edge. The width of the device at the shoulder portions and at its widest point is such that the device may be wrapped up and partially over the shoulders and proximate to the neck of a patient lying in a supine position.

In one example, the device is filled with many small beads, allowing the device to be pliable and conform to a patient's anatomy.

In another example, the lower portion includes opposed wrist portions which project laterally outwardly near the lower edge of the device. The device has a width dimension at the wrist portions that allows the device to be wrapped upwardly to provide lateral support for a patient's hands, wrists and thighs when the patient is in a supine position.

In yet another example, the opposed lateral edges of the device include a tapered waist portion located between the wrist portions and a point proximate the midline to give the device a low profile in the vicinity of the patient's wrists, forearms and lower lateral abdomen so as to provide greater surgical access in these areas, IV access, and access for surgical instruments.

In yet another example, the upper portion provides an adjustable pillow portion to support the patient's neck and head.

A method of supporting the patient in a supine position includes positioning a flexible air-impermeable shell between a patient and a support, such as an operating table. The shell has an upper edge and a lower edge and opposing first and second lateral edges extending between the upper edge and lower edge. The shell defines a laterally extending midline extending between the opposing lateral edges, and includes first and second shoulder support regions positioned adjacent the upper edge and a longitudinally recessed perineal access region adjacent the lower edge. When the patient is in the supine position, the first and second shoulder support regions are folded upwardly to at least partially engage each of the patient's shoulders. The shell is then substantially evacuated such that the first and second shoulder support regions support and retain in place each of the patient's respective shoulders.

In another example, a method of supporting a patient includes urging first and second upper arm support regions of the shell to at least partially engage each of the patient's respective upper arms, such that when the shell is evacuated the first and second upper arm support regions at least partially matingly engage each of the patient's upper arms.

In a further example, a method of supporting a patient includes adjustably inflating the pillow portion to provide appropriate support for the patient's head and neck.

In another example, a surgical positioning device for positioning the body of a patient in a selected position includes first, second, and third chambers. Each has an air-impermeable top wall joined with an air-impermeable bottom wall and top edges, bottom edges, and lateral edges. The second and third chambers are positioned on opposing sides of the first chamber such that at least a portion of one of the lateral edges of the second chamber is positioned adjacent a portion of one of the lateral edges of the first chamber, and at least a portion of one of the lateral edges of the third chamber is positioned adjacent a portion of a different lateral edge of the first chamber.

In another example, at least a portion of the bottom edge of the second chamber is positioned adjacent an edge of the first chamber, and at least a portion of the bottom edge of the third chamber is positioned adjacent a different edge of the first chamber. Each of the first, second, and third chambers can include separate valve systems, allowing for independent evacuation of air from the respective chambers. Each of the valve systems can also include a locking member configured to restrict movement of the valve systems to an open configuration that allows ingress of air into the respective chamber.

In some examples, a single sheet of air-impermeable material forms the top walls of the first, second, and third chambers, and a single sheet of air-impermeable material forms the bottom walls of the first, second, and third chambers. The first chamber can also include an upper portion that extends between a laterally extending midline and the upper edge of the first chamber and a lower portion that extends between the laterally extending midline and the lower edge of the first chamber. The second and third chambers can be positioned on opposing sides of the upper portion of the first chamber.

In another example, opposing strap-receiving members can be positioned at opposing lateral edges of the lower portion of the first chamber, and the strap-receiving members configured to receive a strap to secure the patient and positioning device to an operating table. The lower portion can also include opposing first and second hand and/or wrist support regions that are positioned laterally outward of a central region and adjacent a lower edge of the lower portion for supporting the patient's respective hands and/or wrists. In some examples, a plurality of strap patches can be secured to the bottom wall of the first chamber for receiving a plurality of straps to secure the surgical positioning device to an operating table. Also, a head support region can be provided adjacent to and generally centered relative to an upper edge of the first chamber and an open perineal access region can be provided at a bottom edge of the first chamber, the access region being generally centered relative to the bottom edge.

In some examples, a plurality of beads can substantially fill each of the first, second, and third chambers and the beads can be configured to allow the chambers to remain pliable until air is evacuated from a respective chamber.

In another example, a surgical positioning device includes a flexible and air-impermeable shell comprising an air-impermeable top wall joined with an air-impermeable bottom wall to define a plurality of chambers. Each of the chambers can include a peripheral edge that extends around the periphery of the respective chamber. The plurality of chambers can include a first shoulder chamber, a second shoulder chamber, and a main chamber. The main chamber can include a central region and upper region for supporting at least a portion of a torso of the patient, with the upper region extending between the first and second shoulder chambers so that the first and second shoulder chambers extend laterally outward of the upper region for supporting the patient's respective shoulders. At least a portion of a lateral edge of the first shoulder chamber can be adjacent to a portion of a lateral edge of the main chamber and at least a portion of a lateral edge of the second shoulder chamber can be adjacent to a portion of another lateral edge of the main chamber. Also, at least a portion of bottom edges of the first and second shoulder chamber can be adjacent to portions of the peripheral edge of the main chamber.

In one example, the main chamber can include a separate valve system from the first and second shoulder chambers, such that air can be evacuated from the main chamber independently of the first and second shoulder chambers. A locking member for the valve systems can be provided. The locking member can be configured to restrict movement of the valve systems to an open configuration that allows ingress of air into a respective chamber.

In some examples, opposing strap-receiving members can be positioned at opposing lateral edges of the central region of the main chamber, with the strap-receiving members being configured to receive a strap to secure the patient and positioning device to an operating table. A plurality of strap patches can also be secured to the bottom wall for receiving a plurality of straps to secure the surgical positioning device to an operating table.

In other examples, a head support region can be provided adjacent to and generally centered relative to an upper edge of the main chamber and an open perineal access region can be provided at a bottom edge of the main chamber, the access region being generally centered relative to the bottom edge. A plurality of beads can substantially fill each of the main chamber, the first shoulder chamber, and the second shoulder chamber, with the beads being configured to allow the chambers to remain pliable until air is evacuated from a respective chamber.

In another example, a method of supporting a patient in a supine position with a surgical positioning device is provided. The method includes positioning a flexible and air-impermeable shell having a plurality of chambers between a patient and a support, the plurality of chambers including a main chamber and opposing first and second shoulder chambers; urging the first and the second shoulder chambers to at least partially engage each of the patient's respective shoulders; substantially evacuating the main chamber such that the main chamber engages and at least partially immobilizes a torso of the patient; substantially evacuating the first shoulder chamber such that the first shoulder chamber at least partially engages one of the patient's respective shoulders; and substantially evacuating the second shoulder chamber such that the second shoulder chamber at least partially engages another of the patient's respective shoulders.

In some examples, the main chamber is evacuated before the evacuation of the first and second shoulder chambers. In other examples, the method includes forming irregular surfaces at peripheral edges of the main chamber by the evacuation of the main chamber and forming irregular surfaces at peripheral edges of the first and second chambers by the evacuation of those chambers. The main chamber is positioned between the first and second shoulder chambers so that the irregular surfaces of each of the first and second shoulder chambers engage and interlock with adjacent irregular surfaces on the main chamber to restrict relative movement between the main chamber and the first and second shoulder chambers.

In some examples, the main chamber includes opposing first and second hand and/or wrist support regions. The method can also include urging the first and the second hand and/or wrist support regions to at least partially engage each of the patient's respective hands and/or wrists, wherein upon substantially evacuating the shell, the first and the second hand and/or wrist support regions at least partially matingly engage each of the patient's respective hands and/or wrists.

In some examples, each of the chambers can include a valve system to permit independent evacuation of the respective chambers. The method can include securing the valve systems in a locked position to restrict ingress of air into the respective chambers. The act of securing the valve systems can include positioning a C-shaped lock member on the valve systems to restrict movement of the valve systems into an unlocked position.

In another example, securing the shell to the support can include using at least one fastening strap that is coupled to a bottom wall of the shell. In other examples, the method can include securing the patient and the shell to the support after evacuating all of the chambers by positioning a strap around the patient and through at least two strap-receiving members provided at lateral edges of the main chamber.

The foregoing and other objects, features and advantages of the invention will become more apparent from the following detailed description, which proceeds with reference to the accompanying figures.

DETAILED DESCRIPTION

This disclosure makes reference to the accompanying drawings which form a part hereof, wherein like numerals designate like parts throughout. The drawings illustrate specific embodiments, but other embodiments can be formed and structural changes can be made without departing from the intended scope of this disclosure. Directions and references (e.g., up, down, top, bottom, left, right, rearward, forward, etc.) can be used to facilitate discussion of the drawings but are not intended to be limiting. For example, certain terms can be used such as "up," "down,", "upper," "lower," "horizontal," "vertical," "left," "right," and the like. These terms are used, where applicable, to provide some clarity of description when dealing with relative relationships, particularly with respect to the illustrated embodiments. Such terms are not, however, intended to imply absolute relationships, positions, and/or orientations. For example, with respect to a positioning system, an "upper" surface or portion can be a "lower" surface simply by altering the position of the positioning such as by placing the positioning system on a tilted operating room table. Nevertheless, it is still the same surface and the object remains the same. As used herein, "and/or" means "and" as well as "and" and "or."

Accordingly, this detailed description shall not be construed in a limiting sense, and following a review of this disclosure, those of ordinary skill in the art will appreciate the wide variety of systems that can be devised and constructed using the various concepts described herein. Moreover, those of ordinary skill in the art will appreciate that the exemplary embodiments disclosed herein can be adapted to various configurations without departing from the disclosed concepts. Thus, in view of the many possible embodiments to which the disclosed principles can be applied, it should be recognized that the above-described embodiments are only examples and should not be taken as limiting in scope.

Figure 1:
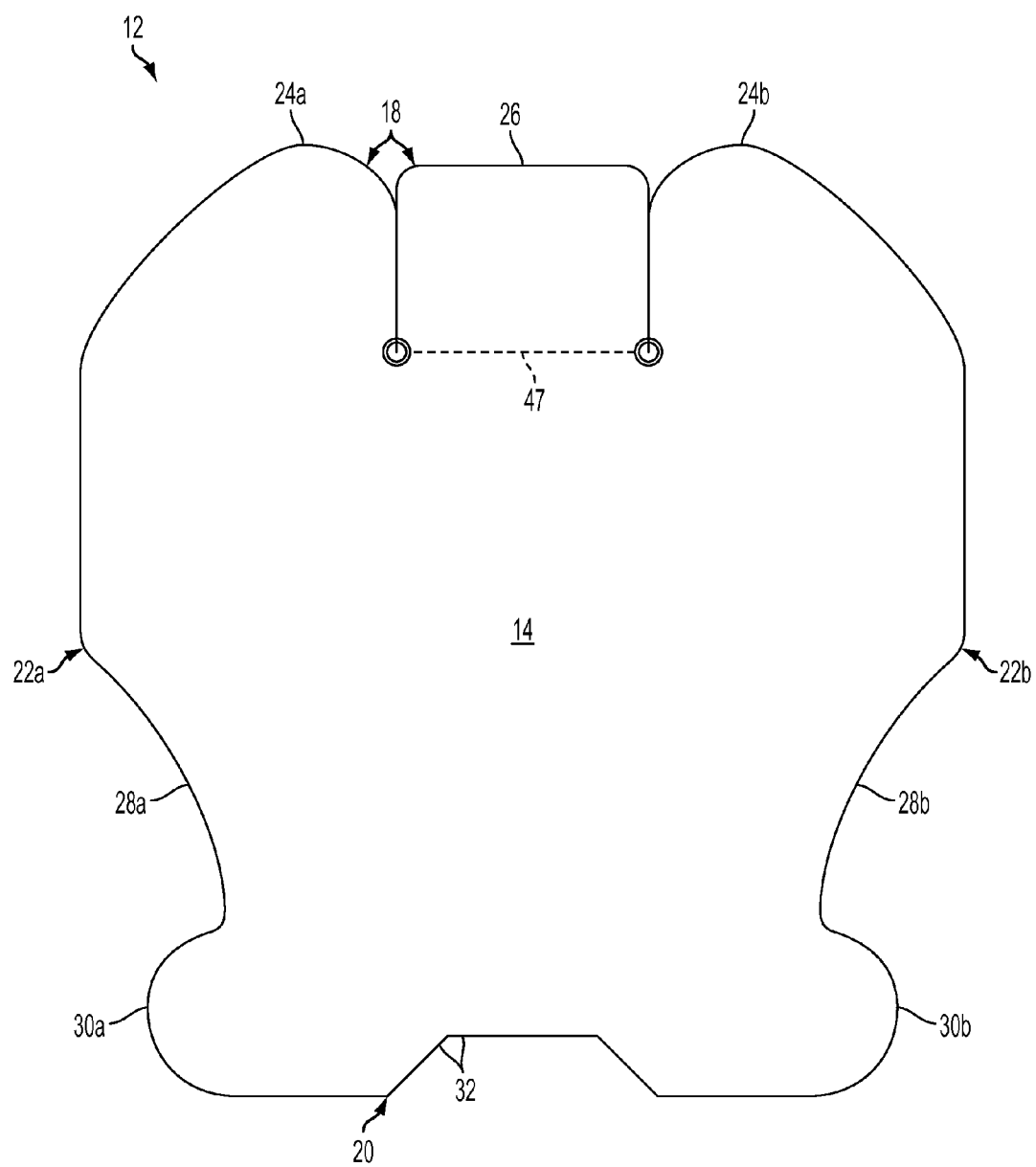
FIG. 1 is a top plan view of an embodiment of a surgical positioning system.
Figure 2:
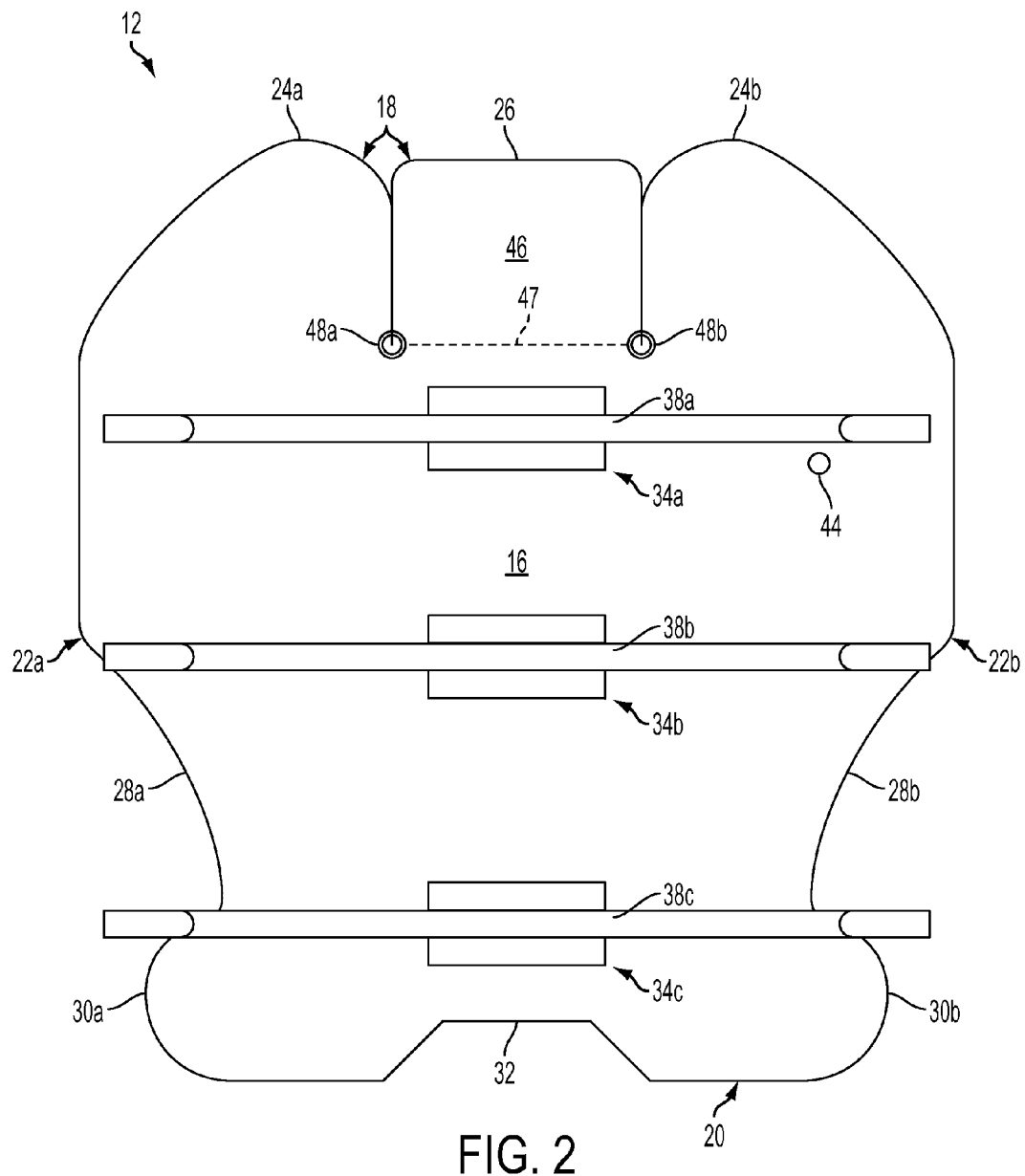
FIG. 2 is a bottom plan view of the embodiment of FIG. 1.

Referring to FIGS. 1 and 2, a surgical positioning system described herein includes a generally flat bag 12 fabricated of flexible, air impermeable material. The bag preferably is about 1½ to 2½ inches thick. One suitable material is "Rocheux Supreme" polyvinyl waterbed film, distributed by Rocheux International, Inc., Carson, Calif., although other materials having similar physical properties may be used. The Rocheux material has desirable low temperature, tear, heat sealing and flexing qualities, as well as superior hydrostatic resistance which makes it particularly suitable for the present positioning system. It also has good resilience, returning quickly to its prior conformation, thereby holding the patient more securely. It is mildew-, bacteria-, puncture- and fire-resistant. Its physical properties are specifically as follows:

| | | |
|---|---|---|
| Thickness (inches) | 0.024, +5%, −0 | ASTM D-751 |
| Embossing | Plain | |
| Weight (oz./yd.$^2$) | 17.5 (min.) | ASTM D-751 |
| Volatility (% loss) | 1.5 (max) | ASTM D-1203-86, Method B |
| Elongation (%) | 350-360 (min) | ASTM D-882 |
| Elongate change after 14 days × 150° F. (%) | Less than 10 | ASTM D-882 |
| Breaking strength factor (psi) | 44 | ASTM D-882 |
| Tensile change after 14 days × 150° F. (%) | Less than 10 | ASTM D-882 |
| Graves tear (lbs.) | 5.6 (min) | ASTM D-1004 |
| Low temperature (° F.) | −20 (min) | ASTM D-1790 |
| Dimensional stability (%) | −5 (max) | ASTM D-1204 |
| Specific gravity | 1.21-1.23 | ASTM D-792 |
| Mildew resistance | Passes ATCC No. 6275 | California Bureau of Home Furnishings, Bulletin 128 |
| Bacteria resistance | Passes ATCC No. 6538, 4352 | California Bureau of Home Furnishings, Bulletin 128 |
| Hydraulic resistance (psi) | 75 | ASTM D-75 1 |
| Puncture resistance (lbs.) | 34.3 | California Bureau of Home Furnishings, Bulletin 100 |

In another preferred embodiment, the flexible impermeable material can be a urethane material.

Figure 4:
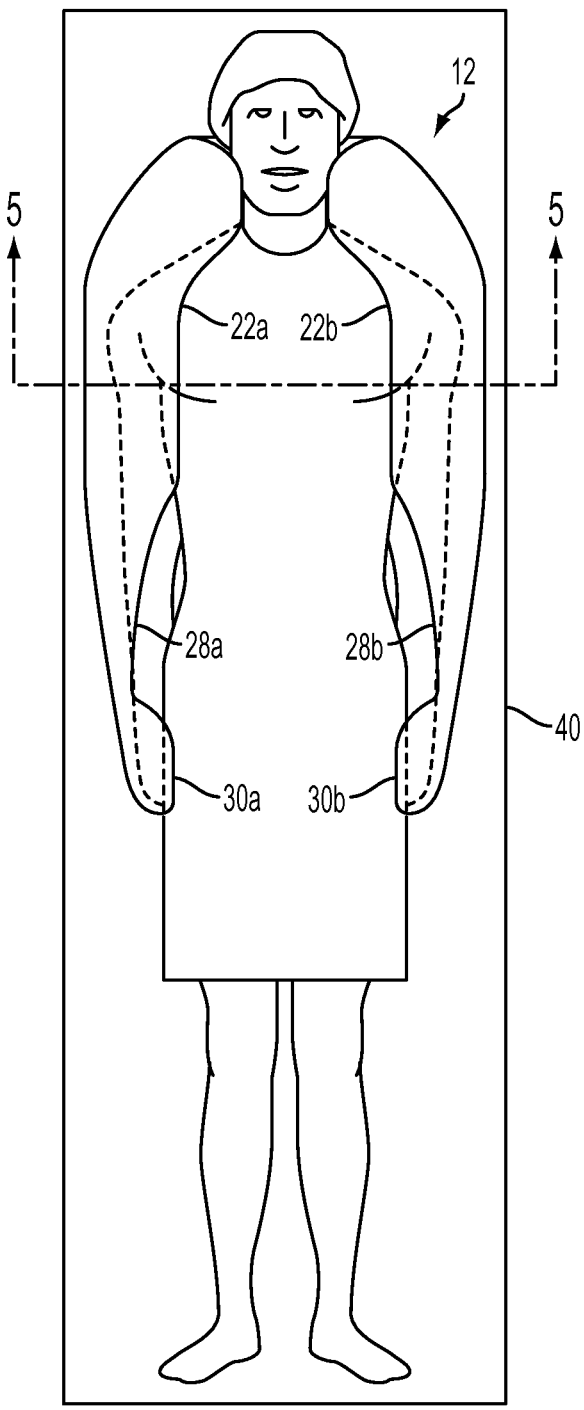
FIG. 4 is a top plan view of the FIG. 1 embodiment, patient and operating table.

The bag 12 includes top and bottom opposing walls 14, 16 which are radio frequency welded, heat sealed or otherwise joined together at their upper, lower and lateral edges 18, 20, 22 for strength and airtightness. The bag's preferred width at its widest point is about 42 inches, which exceeds the shoulder width of most patients. The bag's preferred length at its longest point is about 46 inches, which corresponds generally to the distance between the neck and upper thighs of an average height patient. Thus, when the patient is placed in the supine position on the bag 12, as shown in FIG. 4, the lateral edges 22 can be folded up along the patient's neck, shoulders, arms, hips and upper thighs and packed snuggly against the patient's body to accommodate the natural contours thereof.

Referring again to FIGS. 1 and 2, the upper edge 18 includes two opposed shoulder edge portions 24a, 24b, and a pillow edge portion 26 located therebetween. Adjacent to the pillow edge portion 26, the shoulder edge portions 24a, 24b have a relatively tight radius of curvature, preferably about 4⅜ inch, allowing the upper edge 18 to be folded upwardly adjacent either side of the patient's head and neck for support. As upper edge 18 extends laterally outwardly toward edges 22, the upper edge retains an arc-like curvature but the radius of curvature of shoulder edge portions 24a, 24b increases significantly, preferably to about 22 to 23 inches, to expand the width of the bag and allow the upper edge (when folded) to wrap around and at least partially overlie the patient's shoulders to support and immobilize the patient's upper body. The shoulder portions 24a, 24b of the upper edge 18 terminate where lateral edges 22a, 22b begin, defining the widest point of the bag.

Lateral edges 22a, 22b each define opposed cut-out portions 28a, 28b, and opposed projecting wrist supporting portions 30a, 30b. Wrist supporting portions 30a, 30b project outwardly to increase the width of the bag in the region proximate the lower edge 20. The width of the bag across the wrist supporting portions preferably is about 35 inches. The wrist supporting portions may be folded upwardly to provide lateral support for the patient's wrists and hands. They help secure the patient's wrists and hands against the side of the patient's body. The cut out portions 28a, 28b give the bag a tapered waist and low profile in the vicinity of the patient's arms so as to provide easy access to the patient's wrists and forearms for insertion of an IV, surgical access to the lower lateral abdomen, access for surgical instruments and other purposes.

The lower edge 20 preferably includes a central trapezoid-like cut out 32 to provide perineal access. The cut out 32 preferably conforms to perineal access cut outs sometimes used in operating room table designs to provide access for speculums, rectal instruments and the like.

As shown in FIG. 2, a plurality of strap patches 34a, 34b, 34c (three shown) are secured by heat sealing, radio frequency welding or otherwise to the bottom wall 16. The patches preferably are centered and spaced apart along the bag's longitudinal centerline/axis. Before the strap patches are attached to the bottom wall, an elongate fastener strap 38a, 38b, 38c, is attached, preferably by sewing or other fixed attachment method, to each patch 34a, 34b, 34c. FIG. 2 shows the ends of each strap doubled back on each other for purposes of illustration. The fastener straps 38a, 38b, 38c (FIGS. 7, 8) secure the bag 12 to an operating table 40 (FIG. 4) on which the bag and patient are supported. Each strap has a fastening means to fasten one end of the strap to the other or, when looped around an anchor, to itself to safely secure the bag 12 to the operating table and thereby prevent the bag from sliding relative to the operating table. The fastening means preferably includes Velcro® brand hook-and-loop fastening means or equivalent hook-and-loop fasteners, although adjustable buckle style, clip and other tie down straps will suffice. More specifically, each end of the straps may be looped around an operating table side rail, D-ring or other anchor structure on the table 40, and then secured back to itself using hook-and-loop fasteners or other fastening means. Alternatively, the two ends of each strap may be secured to one another along the underside of the operating table 40, depending on the design of the table.

In another embodiment, the straps can be formed of ballistic nylon. Also, instead of a Velcro®-type fastener, a buckle or other such fastening system (e.g., a D-Ring system, etc.) can be used to secure the ends of the straps to one another.

It will be appreciated that once the straps are secured to the operating table, the fixed attachment of the straps to the strap patches 34a, 34b, 34c (and effectively to the bag 12 as well), keep the bag from sliding laterally on the operating table as, for example, when the table is tilted laterally to place the patient in the Trendelenburg and Lateral Oblique position.

Figure 5:
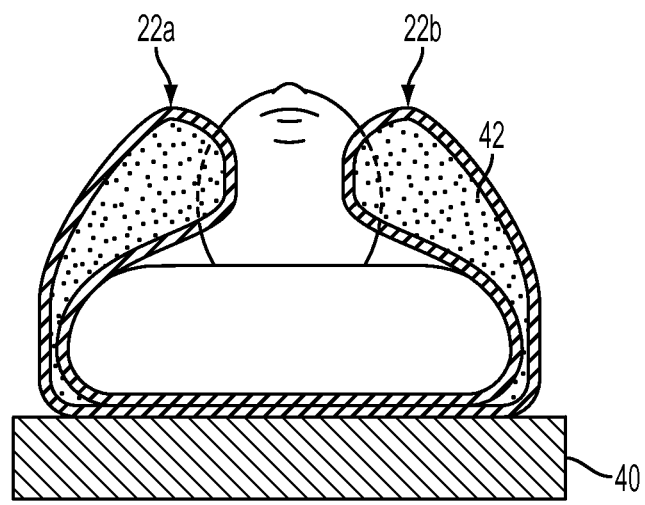
FIG. 5 is a sectional view taken along line 5-5 in FIG. 4.

Before walls 14, 16 are joined together to form the enclosed bag 12, the bag is filled with a charge of elastically deformable plastic beads 42 (FIG. 5). The beads preferably are made of expanded plastic materials, such as polystyrene or polyvinyl chloride, because of their high mechanical strength, elastic deformability and low specific gravity. Beads 42 of expanded polystyrene are especially preferred. When the bag 12 is in the unevacuated condition, the beads 42 remain loose within the bag such that the upper, lower and lateral edges of the bag can be easily moved or folded up along the side of the patient's neck, shoulder, arms, hips and upper thighs to cradle and support the patient in the selected position. The bag preferably is configured to wrap around and overlie at least a portion of the patient's shoulders and upper chest, as shown in FIG. 4.

Figure 6:
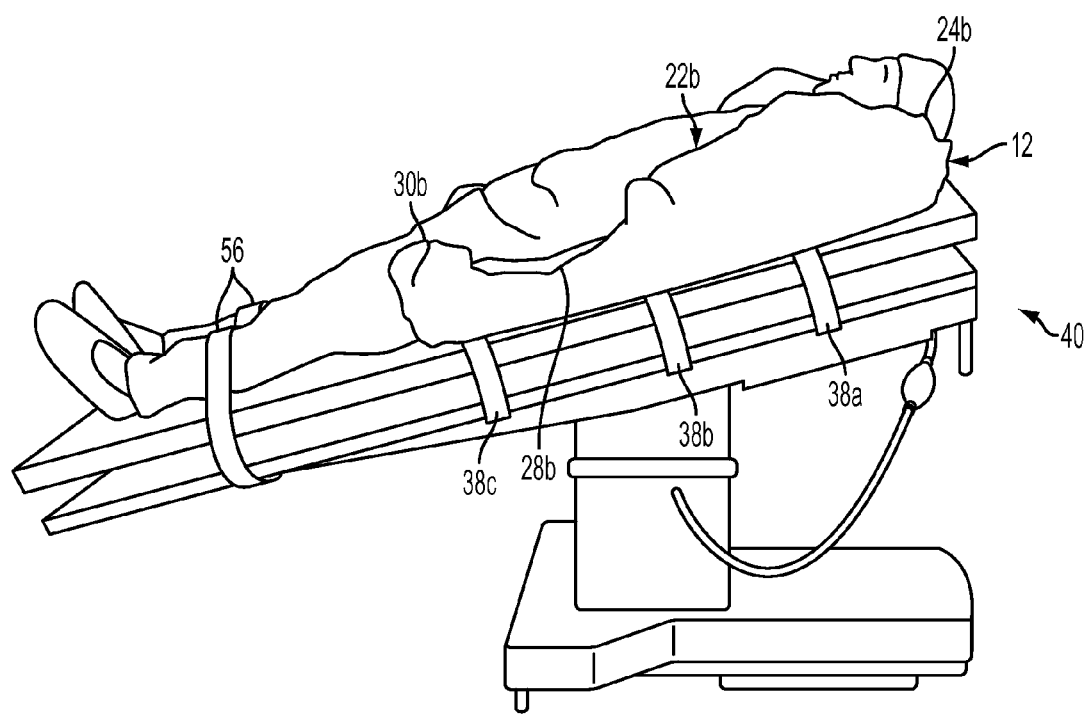
FIG. 6 is a perspective view of the FIG. 1 embodiment and showing a patient in the Reverse Trendelenburg position.
Figure 7:
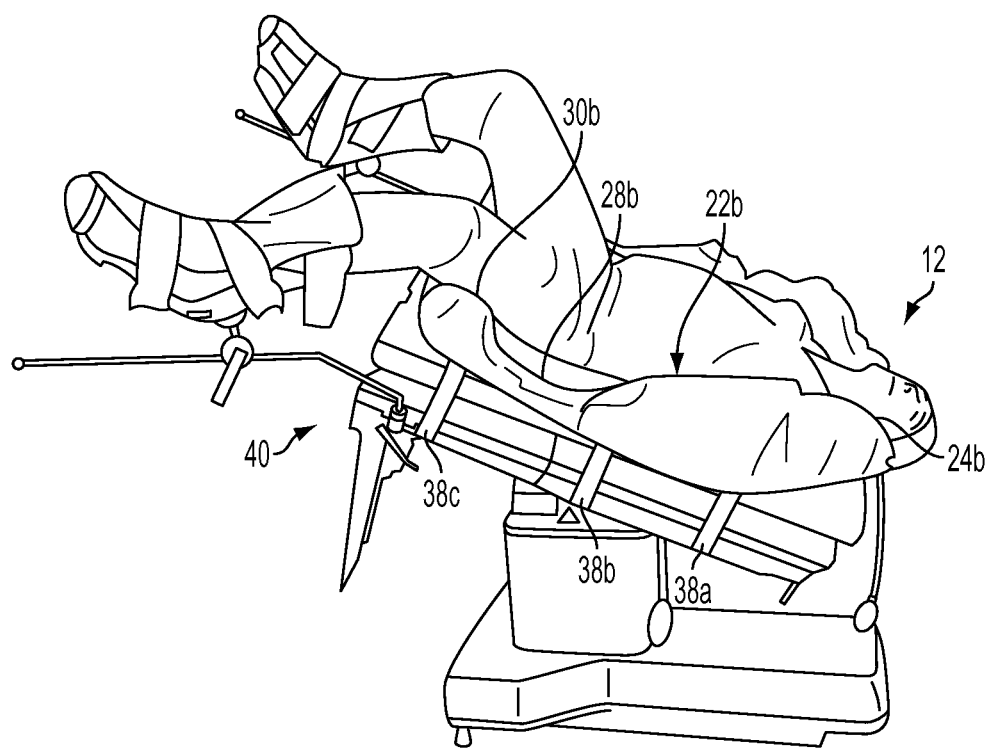
FIG. 7 is a perspective view of the FIG. 1 embodiment and showing a patient in the Trendelenburg as well as Lateral Oblique position.

The bottom wall 16 of the bag 12 is provided with a valve 44 (FIG. 2) which communicates with the interior of the bag for evacuating air therefrom. The valve 44 may be identical or similar to the one described in U.S. Pat. No. 5,906,205, the disclosure of which is herein incorporated by reference. The valve may have a male portion with a protruding valve stem and a plastic tube which connects the valve stem to the bottom wall 16 in an airtight manner. The valve also preferably includes a female portion that may be releasably placed over the male portion to depress the valve stem and open the valve to allow ingress or egress of air. When a source of vacuum is attached to the female portion, air is withdrawn from the interior of the bag. This causes the plastic beads 42 to be packed (or to congregate) into a tight configuration, conforming to the patient's body, as shown in FIGS. 6 and 7. When the female portion is removed from the male portion, the valve closes and no air can enter or exit the bag, thereby maintaining the conformity of the bag to the patient's body. When the patient is to be released, the female portion of the valve 44 (without the vacuum hose attached) is placed over the male portion. This opens the valve 44, thereby allowing air to enter the bag and loosening the configuration of the beads so that they reside in a more relaxed, fluid state. This allows the bag to flatten. It will be appreciated that a variety of conventional valves can be used to withdraw air from the bag, maintain the bag in an evacuated state and allow air to reenter the bag.

Figure 3:
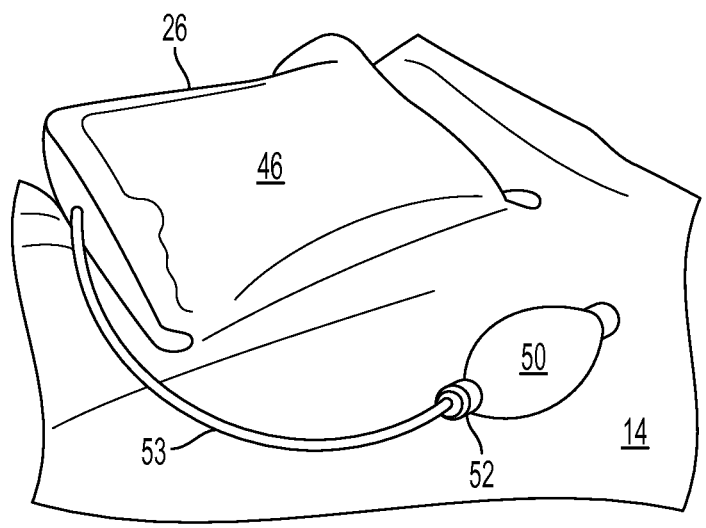
FIG. 3 is a perspective view of one portion of the FIG. 1 embodiment.

As shown in FIGS. 1, 2 and 3, the bag 12 includes an inflatable pillow 46 which is attached to a cut out portion in the bag located centrally along upper edge 18 between shoulder edge portions 24a, 24b. There is no fluid communication between the interiors of the bag 12 and pillow 46, each of which constitutes an air impermeable compartment of its own. The pillow has a width of about 12 inches in one embodiment of the present positioning system.

As shown best in FIG. 3, the pillow 46 is connected to the bag 12 along a hinge line 47 extending between reinforcement grommets 48a, 48b (FIGS. 1, 2), which preferably is formed by joining the top and bottom walls 14, 16 by heat sealing, radio frequency welding or otherwise. The pillow is free to pivot about the hinge line 47 toward the top wall or bottom wall. The pillow 46 provides support for the patient's head and neck, and may be inflated more or less based on the desired position and orientation for the patient's neck/head during the particular procedure, patient's anatomy and other factors. The pillow may be flipped forward to rest on the top wall 14 to accommodate shorter patients.

The pillow preferably is made of the same material as the bag 12 itself. The pillow may be inflated by a number of conventional techniques, one of which is a hand held inflation bulb 50 (FIG. 3) having a release valve 52 attached to a length of plastic tubing 54 in air-type fluid communication with the interior of the pillow. It will be appreciated that the pillow 46 provides independently adjustable support for the patient's head and neck, allowing the surgeon or nurse to adjust the firmness of the support as well as the position and orientation of the patient's head and neck.

Figure 8:
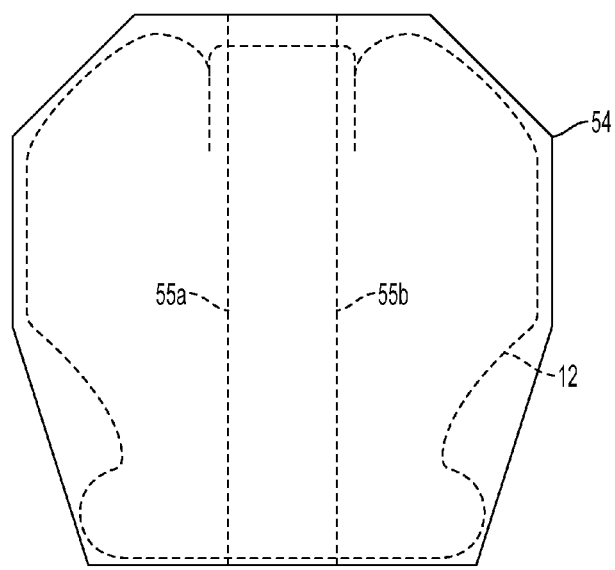
FIG. 8 is a top plan view of a slipcover used in conjunction with the FIG. 1 embodiment.

Referring to FIG. 8, the present positioning system may be provided with a disposable, waterproof slipcover 54 having a size and shape compatible with covering the top wall 14 of the bag 12, a top layer for fully covering the top wall 14 and bottom layer for partially covering the bottom wall 16. The slipcover 54 is provided with slits 54a, 54b that provide side pocket openings in the bottom layer of the slipcover, similar to a throw pillow cover. The openings or pockets allow the sides of the bag to be slipped into the slipcover side pockets such that the top layer of the slipcover covers the top surface of the bag.

Figure 9:
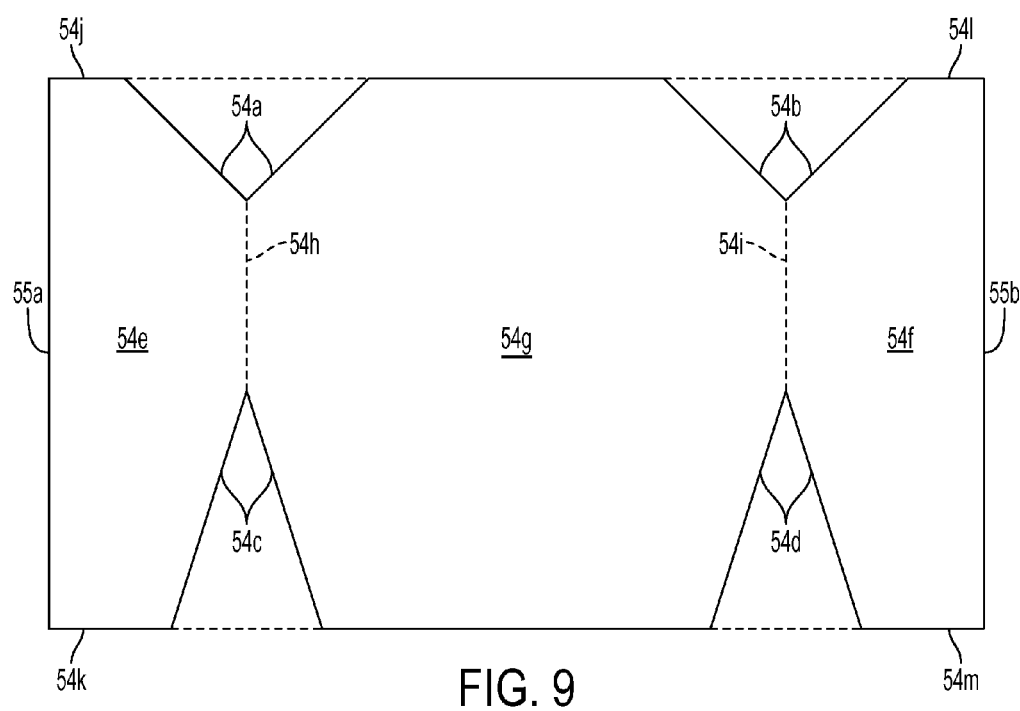
FIG. 9 is a top plan view of a slipcover material with a pattern indicated thereon.

With reference to FIG. 9, the slipcover is formed from a rectangular piece of fabric or material that is cut along cut lines 54a, 54b, 54c, 54d, defining side panels 54e, 54f and central panel 54g. Panels 54e, 54f are then folded underneath central panel 54g along fold lines 54h, 54i, and the edges 54a, edges 54b, edges 54c, and edges 54d are each preferably heat sealed together to create the design shown in FIG. 8. In this way, the panels 54e, 54f form a pair of laterally opposed, two-layer side pockets with respective portions of central panel 54g.

FIG. 4 is a top plan view showing the positioning system supporting the patient in a horizontal position on the operating table 40 during surgery. Air has been evacuated from the bag 12. The positioning system 40 covers the patient's shoulders and provides lateral stabilizing support for the patient's head and neck. Lateral support also is provided for the patient's upper arms, hips and upper thighs, while still providing easy access to the patient's forearms, wrist, and lower lateral abdomen. The pillow 46 supports and orients the back of the patient's head and neck.

FIG. 5 is a transverse sectional view of the positioning system, also in the evacuated condition, taken across the patient's shoulders and upper chest. The positioning system envelopes the patient's upper arms and a portion of the patient's upper chest while providing malleable, comfortable underlying support for the patient's posterior. The positioning system readily conforms to the patient's anatomy.

FIG. 6 is a side elevation view showing an evacuated bag 12, operating table 40 and supine patient in a Reverse Trendelenburg position, with the patient's head elevated above the feet. The patient's lower legs typically are secured to the table by one or more straps. The bag, which conforms closely to the patient's anatomy, cooperates with the straps to comfortably immobilize the patient and resist the force of gravity urging the patient to slide downwardly feet first. A foot board optionally may be placed adjacent the patient's feet. The positioning system partially envelops the patient and creates a friction contact with the patient that must be overcome before the patient may slide relative to the bag and operating table (which are effectively locked together by the straps 38a, 38b, 38c). The conformity of the bag to the contours of the patient's body helps keep the patient from sliding. The wrist supporting portions 30a, 30b, when folded up, support the patient's hands and wrists and also help create a narrow channel in the area of the patient's hips, which is typically smaller than the width of the patient's shoulders, thereby resisting any tendency of the patient to slide down the inclined plane formed by the operating table.

FIG. 7 is a side elevation view showing an evacuated bag 12, operating table 40 and supine patient in a Steep Trendelenburg position, with the patient's feet elevated above her head, and also in a Lateral Oblique position, with the patient tilted laterally to one side. FIG. 7 also depicts the patient with her legs slightly bent and feet spaced apart for certain types of gynecological, laparoscopic, abdominal and urological procedures. It will be apparent that with the patient so positioned the tendency of gravity is to cause the patient to slide downwardly head first on the table and toward one side of the table.

The positioning system envelops the patient's shoulders and a portion of her chest, creating a narrow channel around the patient's neck and shoulders to resist the tendency of the patient to slide either laterally or longitudinally on the inclined plane formed by the operating table. The system provides substantial bulk and mass in the area of the patient's shoulders to help hold the patient in place. The system's conformity to the patient's anatomy (lower back, spine, shoulder blades, etc.) contributes to hold the patient in place.

In using the surgical positioning system, the bag 12 is centered on the operating table 40, with the pillow 46 toward the head of the operating table, and securely fastened to the table using the fastening straps 38a, 38b, 38c. The straps may be secured to the side rails of the operating table. The bag is then smoothed out so that the internal beads 42 inside are evenly distributed. The disposable waterproof slipcover 54 is then placed over the bag 12 and tucked underneath.

The patient is then placed in the supine position on the bag with the neck and head resting on the pillow 46. In the case of smaller or shorter patients, the pillow can be folded forward before the patient is placed in position. The inflation bulb 50 is then used to inflate the pillow as much as necessary to support and position the patient's head/neck, typically in a neutral position for most surgeries.

The lateral sides of the bag are then folded upwardly to engage the sides, shoulders and upper arms, forearms and wrists of the patient. The lateral and superior sides are snugly packed against the patient to accommodate the natural contours thereof and provide a generally U-shaped cradle for the patient. The top of the bag conforms to the patient's posterior. While holding the patient and bag in the desired position, air is evacuated from the interior of the bag 12. Specifically, the female portion of the evacuation valve 44 is attached to the male portion and a vacuum source is connected to the end of the female portion to evacuate air from the interior of the bag. Evacuation is continued until the bag is firm to provide contoured support for the patient. When the desired level of support is achieved, the female portion is detached from the male portion and the vacuum source is detached from the female portion. The bag retains its conforming shape. It will be appreciated that many types of known valve/hose constructions can be used to create and release the vacuum.

Once the patient is secured, the operating table 40 may be inclined to place the patient in the Steep Trendelenburg, Reverse Trendelenburg, Oblique Lateral or other inclined position for surgery. The positioning system uses different techniques to immobilize the patient in a comfortable manner while avoiding the application of significant local pressure to any specific region. The system spreads the cradling/supporting force over a relatively wide surface area of the patient's anatomy and yet provides easy access to a large surface area of the patient's anatomy, including the patient's forearms and lower lateral abdomen. Significantly, the system retains the patient in place by engaging a wide surface area of the patient in a way that eliminates pressure points. The bag's low profile in the vicinity of the patient's forearms also allows surgical instruments to swing lower along the side of the patient and allows the tips of medical instruments in the abdomen to reach the inner aspect of the anterior abdominal wall with less interference from the side restraints of conventional systems. Yet, the positioning system maintains contact with a sizable surface area of the patient's anatomy, including the patient's shoulders, upper arms, forearms, hands, hips and thighs. Such surface contact provides a friction surface and contour fit to resist the tendency of the patient to slip or slide longitudinally relative to the bag.

The bag's overall design also provides protuberances or abutments that serve as longitudinal obstructions for portions of the patient's anatomy. These obstructions resist the gravity influenced tendency of the patient to slide or slip on the inclined operating table. For example, as shown in FIG. 7, the shoulder edge portions of the bag provide a longitudinal and lateral barrier for the shoulders of a patient subject to a gravitational force urging the patient to slide head first or laterally off the operating table. The wrist supporting portions restrain the patient's hands and arms from moving laterally relative to the operating table. As shown in FIG. 6, the wrist supporting portions/projections, when folded up, provide a longitudinal and lateral obstruction for the arms of a patient subject to a gravitational force urging the patient to slide feet first or laterally off the operating table. In this case, the bag 12 also cooperates with leg straps 56, which typically are used to secure the patient's lower legs to the operating table.

The bag also is designed to create narrow channels to resist sliding movement of the patient relative to the bag and the operating table. More specifically, as shown best in FIGS. 4 and 7, the bag defines a relatively narrow channel at the end where the patient's head is placed. The patient's shoulders, chest, and hips have a width dimension that exceeds the width of the head/neck channel associated with the pillow 46. Thus, when the patient is inclined head first, the narrow channel defined at the head end of the bag prevents the wider portions of the patient's anatomy from sliding longitudinally through the channel. The channel effect and shoulder wrap secures the patient even in the steepest Trendelenburg position. In addition, the wrist supporting portions 30a, 30b also define a narrowing channel in the vicinity of the patient's hands and upper thighs. For a patient to slide feet first on the operating table relative to the bag, the patient's hips and shoulders, which are wider than the wrist channel, would have to slide through the narrow channel.

Figure 10:
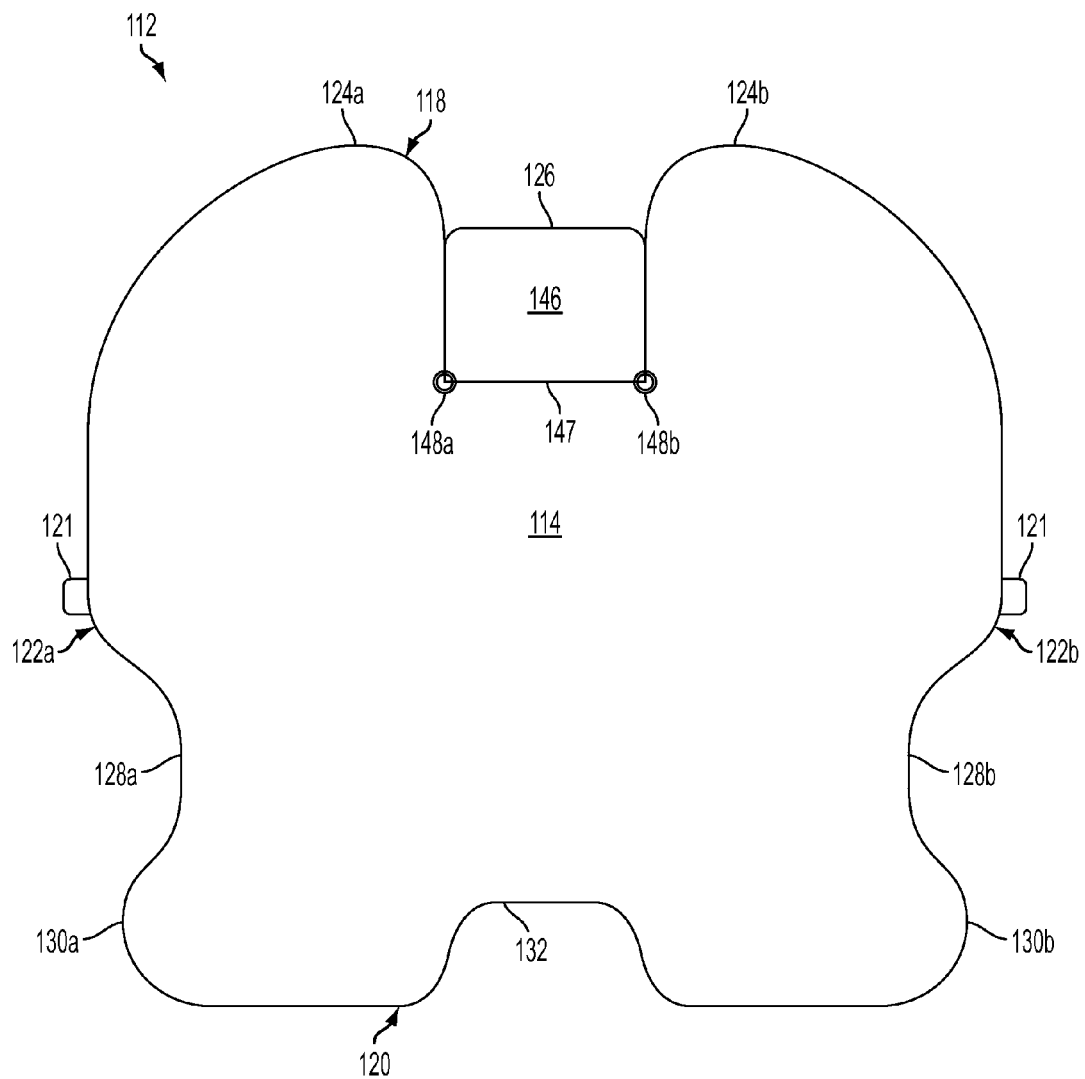
FIG. 10 is a top plan view of an embodiment of a surgical positioning system.
Figure 11:
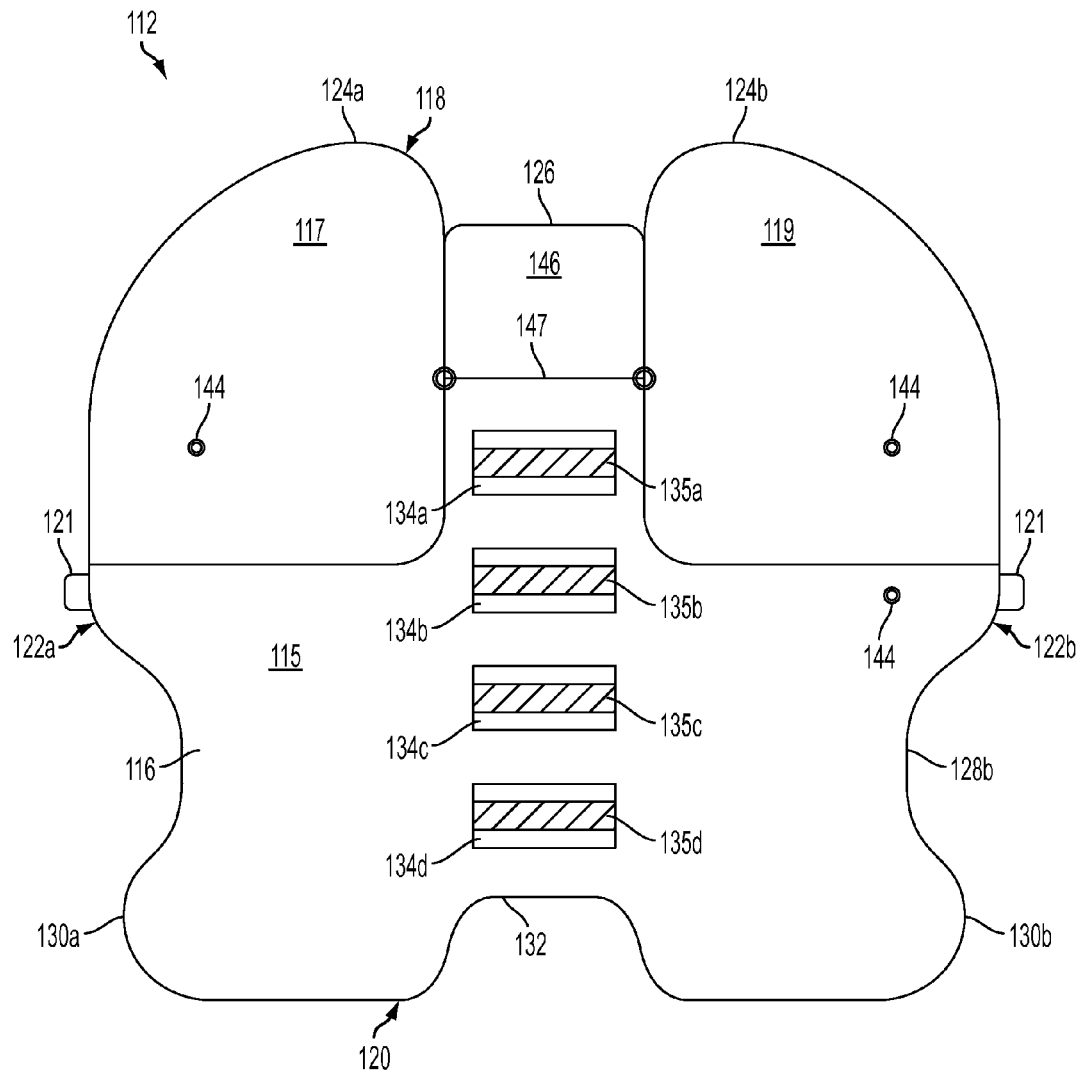
FIG. 11 is a bottom plan view of the embodiment of FIG. 9.

FIGS. 10 and 11 illustrate another embodiment of a surgical positioning system that has multiple chambers. For convenience, elements that are structurally and/or functionally similar to those described above in other embodiments are designed with like reference numbers. Thus, for example, surgical positioning system 112 comprises top and bottom opposing walls 114, 116 that are generally as described above with respect to other embodiments. Top and bottom walls 114, 116 are joined together at their upper, lower and lateral edges 118, 120, 122 for strength and airtightness. As will be understood by the following description, many of the features of the multi-chambered positioning devices described below are common and/or similar to those of the single-chambered positioning devices described above. Moreover, as will be understood by one of ordinary skill in the art, many features of these devices can be used interchangeably between the multi-chambered and single-chambered devices.

Surgical positioning system 112 includes multiple chambers filled with beads 42 to further facilitate positioning and securing the patient using the positioning system. As shown in FIG. 11, which is a bottom view of surgical positioning system 112, a plurality of chambers are provided in different areas of surgical positioning system 112.

Figure 12:
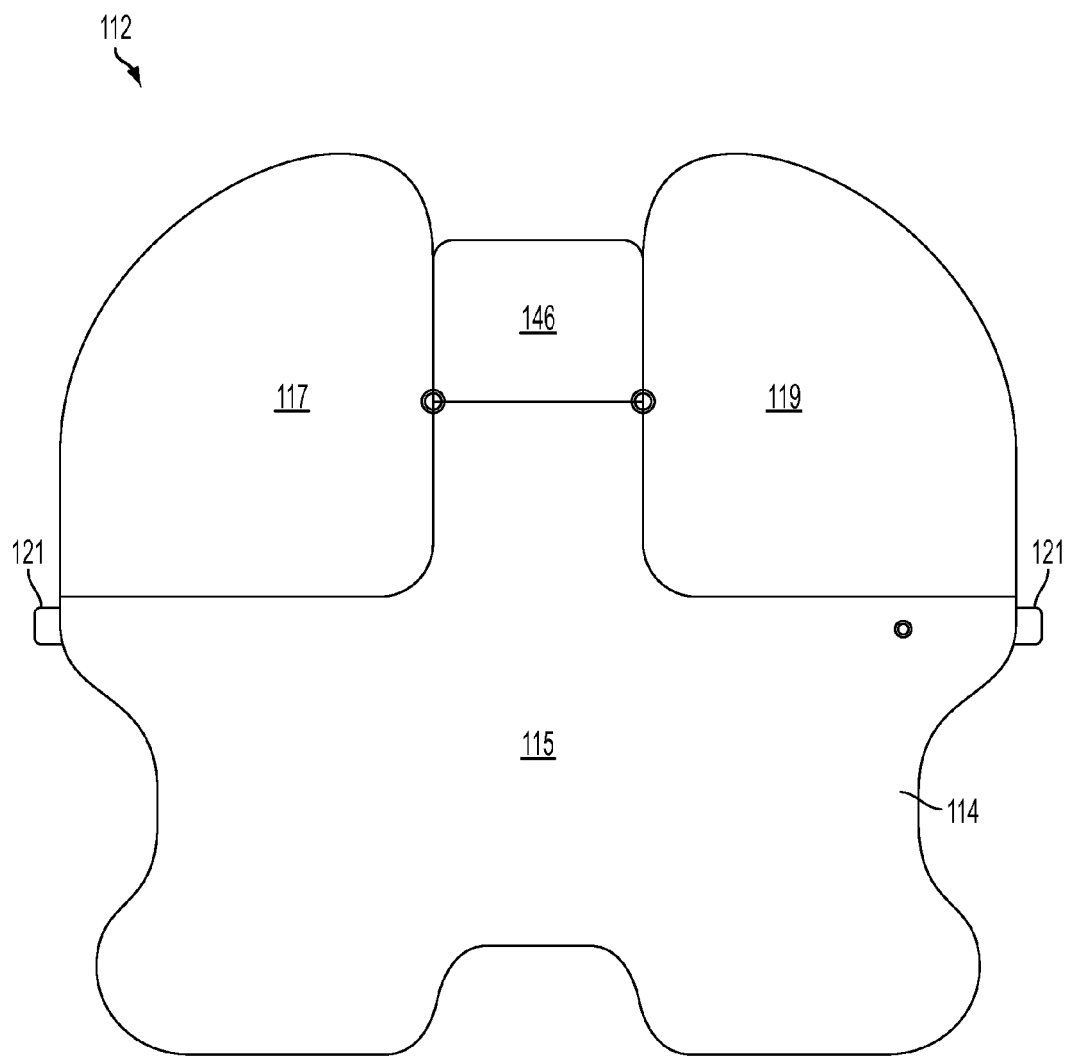
FIG. 12 is a top plan view of an embodiment of a surgical positioning system.

Such chambers can be formed in a variety of manners. For example, in the embodiment shown in FIGS. 10 and 11, the plurality of chambers are formed by sealing portions of bottom walls 116 to top wall 114 (e.g., by heat sealing, radio frequency welding, etc.). By forming the various chambers in this manner, the chambers may only visible from the bottom of the surgical positioning system 112. In other embodiments, however, the various chambers can be formed so that they are visible from both the top and bottom sides of the positioning system 112. For example, FIG. 12 illustrates an embodiment where the different chambers 115, 117, 119 are formed by sealing top wall 114 and bottom wall 116 so that the chambers are visible from the top side of the positioning system 112.

As shown in FIG. 11, a first main chamber 115 is provided in a central and lower area of the surgical positioning system 112. In addition to main chamber 115, secondary chambers 117, 119 are preferably positioned at locations that allow for the creation of greater fixation forces between adjacent chambers to further restrict the movement of the patient relative to the positioning system 112.

By forming a plurality of adjacent chambers of beads 42, a surgical positioning system 112 can be formed with greater rigidity. As described above, in single chamber systems, the beads form a sold mass when air is removed from the chamber. As the solid mass forms, the beads conform to the patient to immobilize the patient in a desired position. In contrast, by forming multiple solid masses by separately evacuating adjacent chambers, not only do each of the solid masses conform to the patient to immobilize the patient in the desired position, but adjacent solid masses also interlock with one another to increase the rigidity of the system.

For example, by evacuating main chamber 115 first, main chamber 115 forms a solid mass that at least partially conforms to the patient. When the solid mass is formed, edges and surfaces of main chamber 115 form irregular surfaces (e.g., bends, folds, crinkles). As air is evacuated from secondary chambers 117, 119, each of those chambers also forms a solid mass that at least partially conforms to the patient. In addition, as each of those solid masses is formed, edges and surfaces of secondary chambers 117, 119 also form irregular surfaces (e.g., bends, folds, crinkles).

As seen in FIG. 11, main chamber 115 has various edges and surfaces that are adjacent to the edges and surfaces of at least a portion of one of secondary chambers 117, 119. After main chamber 115 and secondary chambers 117, 119 are evacuated, those adjacent edges and surfaces of main chamber 115 and secondary chambers 117, 119 are in contact with one another. Because of the irregularities of the surfaces of each of the evacuated chambers, the surfaces of secondary chambers 117, 119 at least partially interlock and/or form a frictional fit with the surface of main chamber 115. Such contact between the adjacent surfaces further increases the rigidity of the positioning system 112 by increasing friction between the adjacent surfaces, thereby restricting relative movement of adjacent chambers. In this manner, the surgical positioning system can be used to further immobilize the patient in anticipation of a surgical procedure.

Secondary chambers can be positioned on positioning system 112 where greater rigidity and strength can be particularly useful, such as at a portion on positioning system 112 where the most pressure is exerted by the patient. For example, when a patient is in the Trendelenburg position, this can be at an upper portion (e.g., shoulder region) of the positioning system 112, where a large portion of the patient's weight is directed.

As shown in FIG. 11, secondary chambers 117, 119 can be provided adjacent the upper portions of main chamber 115. Thus, if the patient is in a Trendelenburg position, with his or her feet above the head, the downward force exerted by the patient can be at least partially countered by the frictional forces between adjacent edges and surfaces of the main chamber 115 and secondary chambers 117, 119. As each of the chambers 115, 117, 119 conform to the patient, surfaces of the chambers contact and engage with surfaces of at least one adjacent chamber to restrict relative movement between adjacent chambers.

Multi-chambered positioning systems can be particularly useful for use with bariatric patients. Bariatric patients are those patients that exceed the physical size, shape, width, and/or weight of an average patient. It is not uncommon for bariatric patients to weigh in excess of 300 pounds and, in some cases, over 400 pounds. Due to the increased forces exerted by a bariatric patient on the support system, the additional rigidity and support provided by the friction forces between adjacent chambers can be particularly helpful to immobilize and position the patient in the manners described above.

In bariatric applications, the positioning system's preferred width at its widest point can be significantly larger than in other applications. Thus for example, instead of about 42 inches, the width of the positioning system can be about 54 inches which exceeds the shoulder width of most bariatric patients. The positioning system's preferred length can also be longer, with its longest point about 51 inches. Thus, when the bariatric patient is placed in the supine position on the positioning system 112, the lateral edges 122 can be folded up along the patient's neck, shoulders, arms, hips and upper thighs and packed snuggly against the bariatric patient's body to accommodate the natural contours thereof.

Referring again to FIG. 10, the upper edge 118 includes two opposed shoulder edge portions 124a, 124b, and a pillow edge portion 126 located therebetween. As shown in FIG. 11, opposing shoulder edge portions 124a and 124b are formed by respective secondary chambers 117, 119. As in other embodiments, adjacent to the pillow edge portion 126, the shoulder edge portions 124a, 124b can extend upward and away from pillow edge portion 126 a distance greater than in other embodiments. For example, in some embodiments, the shoulder edge portions 124a, 124b can extend at least 4 inches, and preferably 5 inches or more, from the pillow edge portion 126.

As in other embodiments, lateral edges 122a, 122b each define opposed cut-out portions 128a, 128b, and opposed projecting wrist supporting portions 130a, 130b. In the example, shown in FIG. 11, secondary chambers do not extend into cut-out portions 128a, 128b; however, it should be understood that different shapes and configuration of secondary chambers are possible.

As shown in FIG. 11, a plurality of strap patches 134a, 134b, 134c, and 134d can be secured by any known manner, including, for example, heat sealing, radio frequency welding or otherwise to the bottom wall 116. As in other embodiments, the patches preferably are centered and spaced apart along the positioning system's longitudinal centerline/axis. Fastener straps such as those shown in FIGS. 7 and 8 can be used to secure the positioning system 112 to an operating table 40 (e.g., FIG. 4) on which the positioning system and patient are supported. Straps can be secured to a respective Velcro® brand hook-and-loop fastener portion 135a, 135b, 135c, and 135d of the strap patches. Alternatively, strap patches can comprise loop portions through which straps can be positioned to secure the positioning system to the table.

It will be appreciated that once the straps are secured to the operating table, the fixed attachment of the straps to the strap patches 134a, 134b, 134c (and effectively to the positioning system 112 as well), keep the positioning system from sliding laterally or longitudinally on the operating table as, for example, when the table is tilted laterally while the patient in the Trendelenburg and other positions.

Additional strap and/or fastening systems can be used to further secure the patient and/or the positioning system to the table. For example, as shown in FIGS. 10, 11, and 12, strap-receiving members 121 can be positioned at the lateral edges 122a, 122b of the positioning system 112. Strap-receiving members 121 can comprise loops or other such devices that are capable of receiving and securing a strap at the lateral edges 122a, 122b. Strap-receiving members 121 can be secured to the lateral edges 122a, 122b in any known manner, such as the heat sealing, radio frequency welding, stitching, etc. Once the positioning system 112 is evacuated so that it conforms to the patient, straps can be passed through the strap-receiving members (e.g., loops), around the patient, and to at least a portion of the operating table to further secure the patient and positioning system 112 to the operating table. Such straps can be particularly helpful when the operating table is tilted laterally as such straps can further restrict lateral movement of positioning system 112 relative to the operating table.

The strap-receiving members 121 shown in FIGS. 10-12 are shown positioned at lateral edges of a main chamber; however, it should be understood that such strap-receiving members 121 can be positioned at other locations on the positioning system 112, including for example, at other points along the lateral edge of the main chamber and at points along other surfaces on the main chamber (e.g., on the top and/or bottom walls). Such strap-receiving members can also be positioned on the secondary chambers 117, 119 and/or adjacent those chambers if desired.

Positioning system 112 preferably is configured to wrap around and overlie at least a portion of the patient's shoulders and upper chest, as described in other embodiments and as shown, for example, in FIG. 4. The straps that extend from strap-receiving members 121 and around the patient can also reduce the width of the positioning system 112 in its evacuated configuration. Thus, for example, if the positioning system 112 has portions that "wing" or extend laterally over the edges of the operating table, the straps can pull those portions of the positioning system 112 inward (i.e., towards the patient), thereby eliminating or reducing the amount that the positioning system 112 extends off the operating table. This can be particular useful when using a larger positioning system with bariatric patients because such positioning systems (and the patients themselves) can be wider than the operating table.

The straps can be secured around or coupled to any available portion of the operating table. For example, the straps can be secured to a side rail or, in other embodiments, can extend around the bottom of the table and be secured to another portion of the table or to itself.

In the exemplary embodiments that include multiple chambers described above, each of the various chambers can be evacuated independently of the evacuation of other chambers. Thus, as described above, main chamber 115 can be evacuated before secondary chambers 117, 119 are sequentially or concurrently evacuated. To permit independent evacuation, each of the chambers 115, 117, 119 can have a valve 144 that communicates with the interiors of the chambers 115, 117, 119 for evacuating air therefrom. Various possible valves are described in more detail above.

Figure 13:
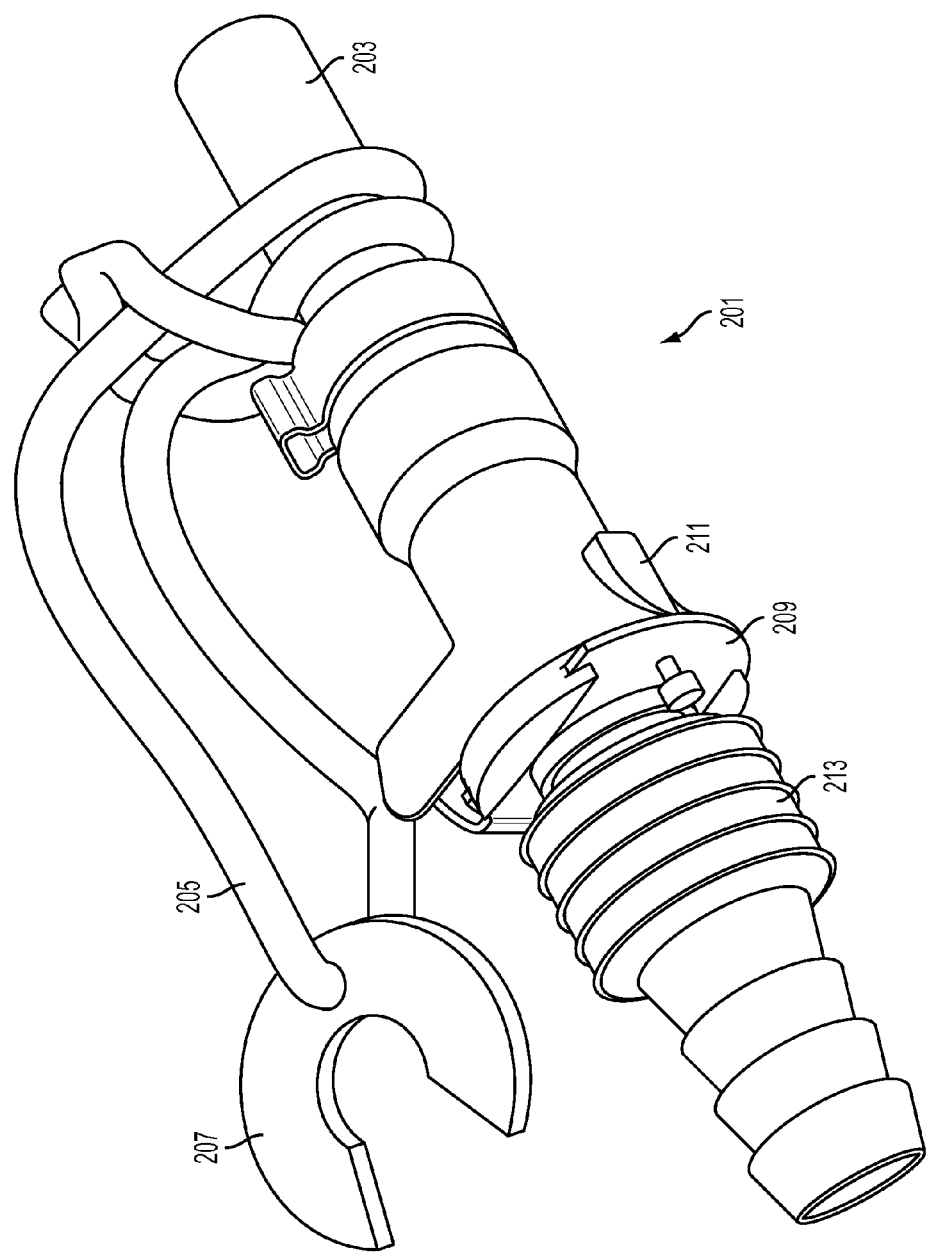
FIG. 13 is a perspective view of a locking mechanism for use with a surgical positioning system, showing the mechanism in an unlocked position.
Figure 14:
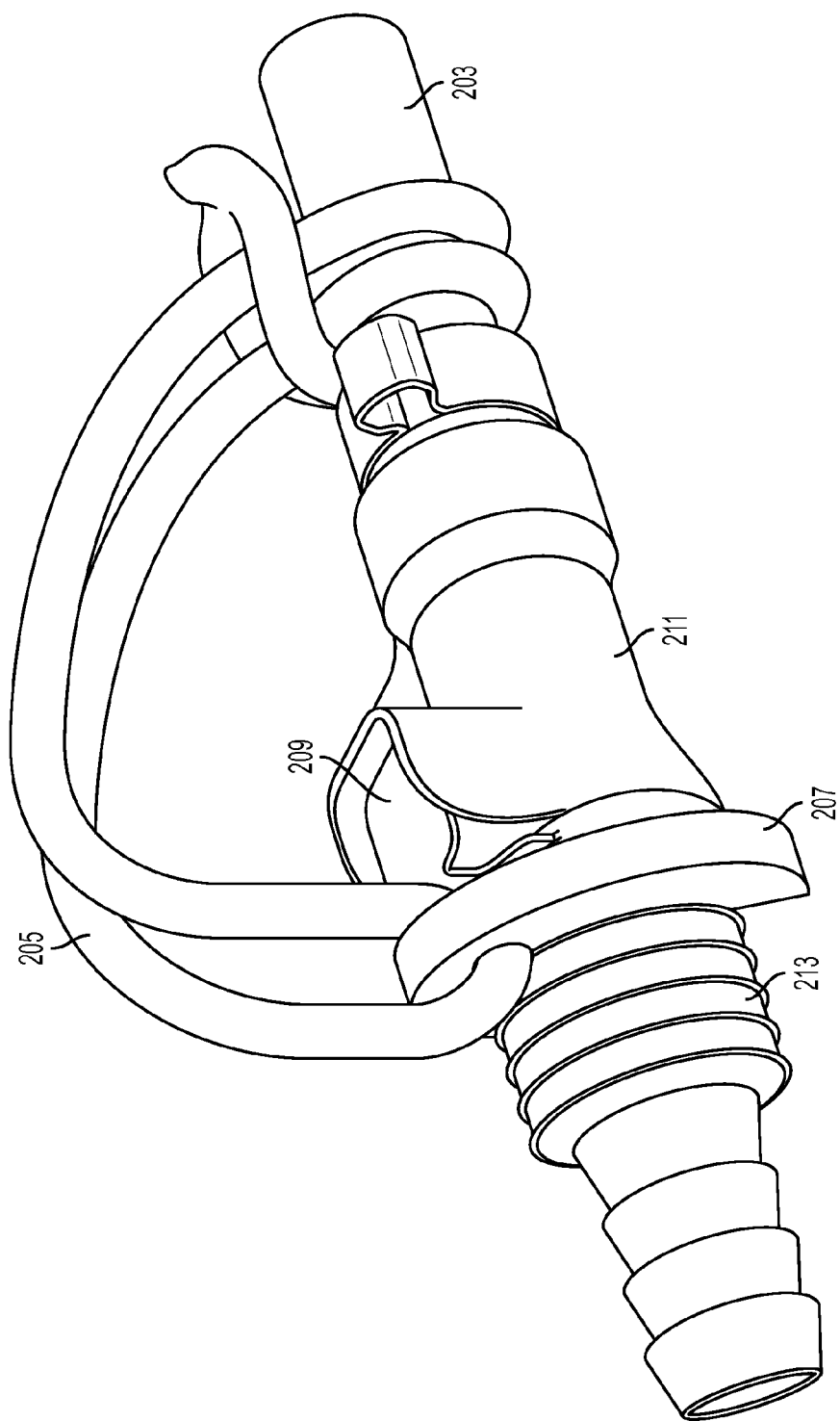
FIG. 14 is a perspective view of a locking mechanism for use with a surgical positioning system, showing the mechanism in a locked position.

A valve lock can also be provided to lock the valve after evacuation to prevent an unintentional and/or accidentally release of the negative pressure applied to the positioning system during operation. FIGS. 13 and 14 illustrate an exemplary valve system 201 that can be moved between an open and a closed position to allow or restrict, respectively, the flow of air into and out of the chambers associated with that valve system 201.

FIG. 13 illustrates a valve locking system that comprises a valve stem 203, a main portion 211, and a moveable member 213 coupled to the main portion 211. Moveable member 213 can be moved inward to open the valve system 201 and allow the ingress and egress of air from the chamber associated with that valve system 201. An intermediate member 209 can be positioned between main portion 211 and moveable member 213, with the intermediate member 209 forming a slot into which a lock member 207 can be received. Lock member 207 can be formed in a C-shape so that it can be received within the slot of the intermediate member 209.

As shown in FIG. 13, when lock member 207 is inserted into the slot formed between main portion 211 and moveable member 213, moveable member 213 cannot be moved inward to the open position. Thus, lock member 207 can secure the valve system 201 in a closed position and the chance of valve system 201 being accidentally opened during a surgical procedure (or at any other undesired time) can be significantly reduced.

At least one port can be provided in one or more of the top and bottom walls 114, 116 to allow for the addition of beads to the positioning system 112. Because of the negative pressures applied to the beads, over time, the beads can deteriorate and lose some functionality. Accordingly, the port allows access to the internal chamber(s) of the system so that additional beads can be added to system. Of course, the port can also allow for the removal or exchange of beads within the positioning system. The port can comprise an opening that has a cover (e.g., a round cap) or removable member capable of allowing access to the opening. Such ports can also be schematically depicted by a square hinged member positioned along any surface of one or more chambers. Port(s) are preferably positioned on the bottom wall 116 of the positioning system so that the port(s) are not located on the side of the positioning system that contacts the patient.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as my invention all that comes within the scope and spirit of these claims.

I claim:

1. A surgical positioning device for positioning the body of a patient in a selected position, the device comprising:
  a flexible and air-impermeable shell comprising an air-impermeable top wall joined with an air-impermeable bottom wall to define a plurality of chambers, each of the chambers comprising a peripheral edge that extends around the periphery of the respective chamber,
  wherein the plurality of chambers include a first shoulder chamber, a second shoulder chamber, and a main chamber,
  the main chamber comprises a central region and upper region for supporting at least a portion of a torso of the patient, the upper region extending between the first and second shoulder chambers so that the first and second shoulder chambers extend laterally outward of the upper region for supporting the patient's respective shoulders,
  at least a portion of a lateral edge of the first shoulder chamber being adjacent to a portion of a lateral edge of the main chamber and at least a portion of a lateral edge of the second shoulder chamber being adjacent to a portion of another lateral edge of the main chamber, and
  at least a portion of bottom edges of the first and second shoulder chamber being adjacent to portions of the peripheral edge of the main chamber.

2. The surgical positioning device of claim 1, wherein the main chamber comprises a separate valve system from the first and second shoulder chambers, such that air can be evacuated from the main chamber independently of the first and second shoulder chambers.

3. The surgical positioning device of claim 2, further comprising a locking member for the valve systems, the locking member being configured to restrict movement of the valve systems to an open configuration that allows ingress of air into a respective chamber.

4. The surgical positioning device of claim 1, further comprising opposing strap-receiving members positioned at opposing lateral edges of the central region of the main chamber, the strap-receiving members configured to receive a strap to secure the patient and positioning device to an operating table.

5. The surgical positioning device of claim 1, further comprising:
a plurality of strap patches secured to the bottom wall for receiving a plurality of straps to secure the surgical positioning device to an operating table.

6. The surgical positioning device of claim 1, further comprising:
a head support region adjacent to and generally centered relative to an upper edge of the main chamber; and
an open perineal access region provided at a bottom edge of the main chamber, the access region being generally centered relative to the bottom edge.

7. The surgical positioning device of claim 1, further comprising a plurality of beads substantially filling each of the main chamber, the first shoulder chamber, and the second shoulder chamber,
wherein the beads are configured to allow the chambers to remain pliable until air is evacuated from a respective chamber.

8. The surgical positioning device of claim 1, further comprising at least one port positioned on the bottom wall and operable between an open and closed configuration to allow for the addition of beads to one or more of the chambers.

9. A method of supporting a patient in a supine position with a surgical positioning device, the method comprising:
positioning a flexible and air-impermeable shell having a plurality of chambers between a patient and a support, the plurality of chambers including a main chamber and opposing first and second shoulder chambers;
urging the first and the second shoulder chambers to at least partially engage each of the patient's respective shoulders;
substantially evacuating the main chamber such that the main chamber engages and at least partially immobilizes a torso of the patient;
substantially evacuating the first shoulder chamber such that the first shoulder chamber at least partially engages one of the patient's respective shoulders; and
substantially evacuating the second shoulder chamber such that the second shoulder chamber at least partially engages another of the patient's respective shoulders.

10. The method of claim 9, wherein the main chamber is evacuated before the evacuation of the first and second shoulder chambers.

11. The method of claim 10, further comprising:
forming irregular surfaces at peripheral edges of the main chamber by the evacuation of the main chamber; and
forming irregular surfaces at peripheral edges of the first and second chambers by the evacuation of those chambers,
wherein the main chamber is positioned between the first and second shoulder chambers so that the irregular surfaces of each of the first and second shoulder chambers engage and interlock with adjacent irregular surfaces on the main chamber to restrict relative movement between the main chamber and the first and second shoulder chambers.

12. The method of claim 9, wherein the main chamber comprises opposing first and second hand and/or wrist support regions, the method further comprising:
urging the first and the second hand and/or wrist support regions to at least partially engage each of the patient's respective hands and/or wrists, wherein upon substantially evacuating the shell, the first and the second hand and/or wrist support regions at least partially matingly engage each of the patient's respective hands and/or wrists.

13. The method of claim 9, wherein each of the chambers comprises a valve system to permit independent evacuation of the respective chambers, the method further comprising:
securing the valve systems in a locked position to restrict ingress of air into the respective chambers.

14. The method of claim 9, wherein the act of securing the valve systems comprises:
positioning a C-shaped lock member on the valve systems to restrict movement of the valve systems into an unlocked position.

15. The method of claim 9, further comprising:
securing the shell to the support using at least one fastening strap that is coupled to a bottom wall of the shell.

16. The method of claim 9, further comprising:
securing the patient and the shell to the support after evacuating all of the chambers by positioning a strap around the patient and through at least two strap-receiving members provided at lateral edges of the main chamber.

* * * * *